United States Patent [19]
Itoh

[11] Patent Number: 5,368,590
[45] Date of Patent: Nov. 29, 1994

[54] CORNEAL SPONGE AND METHOD OF USE

[75] Inventor: Seiji Itoh, Mohara, Japan

[73] Assignee: Katsuhiko Mukai, Kashiwa, Japan

[21] Appl. No.: 52,619

[22] Filed: Apr. 27, 1993

[30] Foreign Application Priority Data

Sep. 29, 1992 [JP] Japan .................. 4-283751

[51] Int. Cl.$^5$ .................................................. A61B 9/00
[52] U.S. Cl. .......................................... 606/4; 606/5;
606/6; 128/853; 128/858
[58] Field of Search ................ 606/4, 5, 6; 128/853,
128/858, 890–893

[56] References Cited

U.S. PATENT DOCUMENTS

| | | | |
|---|---|---|---|
| 4,122,847 | 10/1978 | Craig | 128/858 |
| 4,570,626 | 2/1986 | Norris et al. | 128/858 |
| 5,108,388 | 4/1992 | Trokel | 606/5 |

FOREIGN PATENT DOCUMENTS

| | | | |
|---|---|---|---|
| 0372127 | 6/1990 | European Pat. Off. | 606/4 |
| 9111158 | 8/1991 | WIPO | 606/5 |

*Primary Examiner*—David M. Shay
*Assistant Examiner*—Sonya C. Harris
*Attorney, Agent, or Firm*—Staas & Halsey

[57] ABSTRACT

A sponge which is placed on the cornea for laser treatment to absorb unavoidable exuded fluids from the peribulber. This corneal sponge offers protectiveness, convenience and improved effectiveness of corneal laser therapy. The corneal sponge has a surgical space to expose the portion of the cornea to be treated, and is marked for accurate and easy alignment of the microscopic field. The corneal sponge contains a cool ophthalmic solution used to minimize inflammatory response which may cause postoperative complications such as corneal haze and inconsistent corneal refractions.

10 Claims, 3 Drawing Sheets

CORNEAL SPONGE AND METHOD OF USE

BACKGROUND OF THE INVENTION

To practice corneal ablation, an excimer laser with wavelength of 193 nm has been recently developed. Photorefractive keratectomy has been also investigated and utilized for corneal refractive correction. Phototherapeutic keratectomy, such as corneal leukoma, pterygium, corneal erosion and herpetic keratitis surgeries, can also be performed using the excimer laser. The excimer laser is also used for penetrating and lamellar keratoplasty.

Prior to the excimer photoablation to sculpt corneal stroma, the epithelium of the cornea to be treated is removed manually with a spatula. Prior to the corneal surgery, at least one of the following ophthalmic solutions are administered: antibiotics, miotics, midriatics or anesthetics.

When a lid retractor, which is used to secure the eyelid open, depresses the eyeball, the administered ophthalmic solution is unexpectedly exuded onto the corneal surface along with tears. Such exudation is eliminated by manually applying a conventional sponge or using a drainage tube attached to the temporal lid margin for continuous outflow of the exuded fluids.

This exudation on the cornea interferes with treatment because it reflects some light back into the microscope while absorbing some of the laser's light, thus making corneal ablation less effective.

In order to remove such exuded fluids from the cornea, a stick-type polymeric absorbent, a gauze or drain tubing is used. However, these techniques do not sufficiently or conveniently remove a sudden increase in the amount of exuded fluid, particularly during laser therapy.

As the excimer laser heats the corneal tissue, it causes more inflammatory responses and changes the corneal thickness resulting in a postoperative corneal haze. The patient must, therefore, begin a corticosteroids regimen after the laser surgery to minimize corneal inflammatory response which causes corneal haze.

It is reported that topical steroid use over a few months is potentially hazardous.

Accurate axis alignment is required in excimer laser astigmatism correction to achieve optimal results, and is mandatory in any corneal surgery.

The annular sponge appearing in page 42 and 43 in *Excimer Laser Surgery*, published by Igaku-Shoin Medical Publishers, Inc., New York, is exemplary of prior laser ablation. The annular sponge is placed on the outside of the cornea, because the cornea has to be "marked" for subsequent procedures. The annular sponge is soaked in a topical anesthetic and placed on the eye for marking the center of the pupil by a hook and is removed after the marking is made. An annular sponge used only for anesthesia has a long arm for easier manipulation of the sponge.

SUMMARY OF THE INVENTION

As previously explained, the exuded fluids complicate the surgical procedure, and in order to prevent the exuded fluids from covering the corneal surface during laser surgery, a novel corneal sponge has been designed, as described hereinafter.

The corneal sponge is designed to fit onto a typical corneal surface, absorb the exuded fluids and provide at least one surgical "space" to expose the area of the cornea undergoing treatment. The corneal sponge may be convex or may have notches cut into it to form flaps which will form to fit the corneal surface, improving its adhesive quality.

The corneal sponge of the present invention is made of a water-absorbing material preferably selected from the following group: plastic sponge, cellulose, blotting paper, cotton, carbon fiber and polymeric absorbent.

The laser surgery is performed through the surgical "space" cut away either within or from the perimeter of the corneal sponge. The sponge is placed directly on the cornea in the case of patients needing corneal treatment.

A positioning mark may be provided on the corneal sponge for accurate placement on the cornea and for alignment of the microscopic field. Any mark, such as a notch or print, can be used.

This sponge serves as a reservoir for a cool solution to avoid corneal complications which may be caused by the heat produced by the laser ablation.

In accordance with the teachings of the present invention, the corneal sponge absorbs unavoidable, exuded tears mixed with ophthalmic solution which are exuded onto the corneal surface undergoing laser surgery. For patients needing corneal laser treatment, the corneal sponge Is kept on the cornea to absorb the exuded fluids and to keep dry that portion of the cornea undergoing laser surgery.

Another objective achieved by the present invention is that the corneal sponge can be used as a target marker during alignment of the cornea to be treated.

A still further objective achieved by the present invention is that the surgical space of the corneal sponge isolates the area of the cornea to be treated, thus serving as a laser guide.

A further objective achieved by the present invention is that the corneal sponge contains a reservoir of a cool ophthalmic solution, which protects the corneal surface against heat produced by the laser ablation. That is, during treatment of patients needing corneal laser treatment, the corneal sponge, containing a cooled ophthalimic solution, is placed on the cornea to minimize postoperative inflammation that may cause corneal haze.

BRIEF DESCRIPTIONS OF THE DRAWINGS

DETAILED DESCRIPTION OF THE PREFERRED EMBODIMENTS

The effectiveness of the excimer laser is reduced by unavoidable exuded tears and ophthalmic solution engaging the cornea because such fluids absorb and reflect the laser light. The corneal sponge of the present invention absorbs the exuded fluids and keeps dry the portion of the cornea to be treated. The corneal sponge also shades and protects the rest of the cornea against the laser beam.

The corneal sponge of the present invention also provides at least one positioning mark on the corneal sponge for target alignment of the microscopic field.

Such marks are useful in photorefractive keratectomy, especially in astigmatism surgery which requires accurate axial alignment. Any mark, printed or incised, on the corneal sponge, can be applicable for targeting the microscopic field.

The corneal sponge has a convex configuration, having a radius of curvature of approximately 7 to 8 mm, which permits the sponge to adhere to a congruently shaped cornea. If the corneal sponge has notches cut from the perimeter to form flaps, it is not necessary to have the convex configuration.

The corneal sponge has at least one surgical space cut away therefrom to allow access to the area of the cornea to undergo treatment. The surgical space can be any place and any shape in the corneal sponge.

It is preferred that the surgical space be larger than approximately 1 mm. A diameter of up to approximately 30 mm is preferred as the corneal sponge may otherwise be dislocated by the eyelid or the lid retractor.

Because the average diameter of a human cornea is reported to be approximately 11 to 12 mm, a corneal sponge with a diameter larger than about 12 mm covers the surrounding tissue of the cornea.

As an excimer laser transiently heats the cornea approximately 10 to 15 degrees Centigrade by several hundreds of laser pulses during surgery, corneal inflammation is increased and the change of the corneal thickness occurs. Such symptoms cause corneal haze or inconsistent corneal refractions in photorefractive and phototherapeutic keratectomy.

The corneal sponge can minimize such damage to the cornea by containing a cooling ophthalmic solution. The solution, for example, may be cooled to an ideal temperature of 4 degrees Centigrade. A temperature of the solution between about 2 and 10 degrees Centigrade is preferred to maintain the corneal temperature below the normal temperature during the laser surgery.

The use of postoperative topical steroids can be minimized due to the decreased occurrence of corneal haze. The incidence of steroid glaucoma and steroid cataract 1s thereby reduced.

EXAMPLE I

Figure 1:
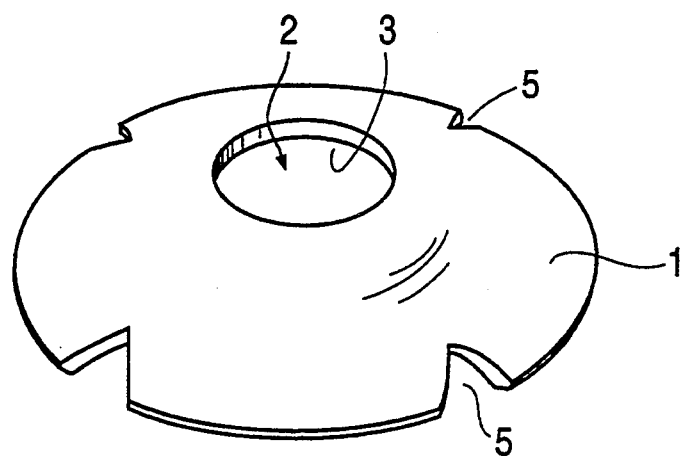
FIG.1 is a perspective view of a preferred embodiment the corneal sponge of the present invention.
Figure 2:
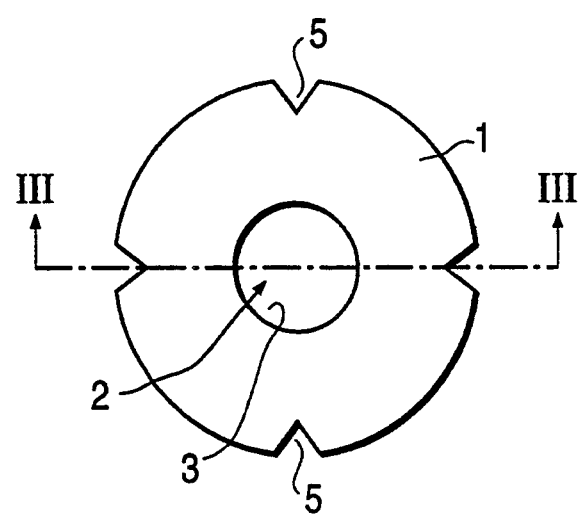
FIG.2 is a plan view thereof.
Figure 3:
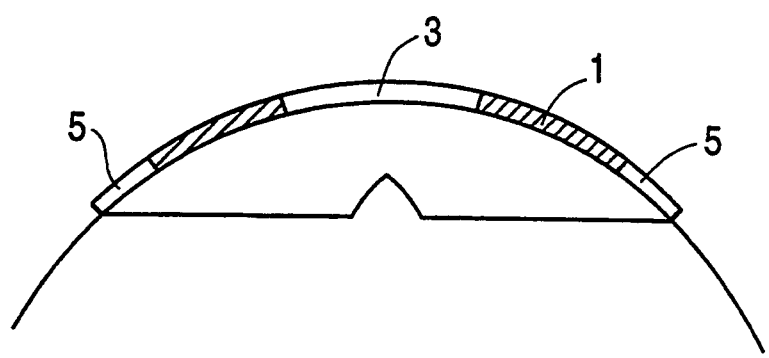
FIG.3 is a sectional view along the line III—III of FIG.2.

FIGS. 1, 2 and 3 illustrate the convex corneal sponge. The corneal sponge (1) is made of polymeric absorbent, is doughnut-like in configuration and has a 11 mm diameter. The sponge is provided with four wedge-shaped notches (5) or positioning marks at every 90 degree position for target alignment, and a surgical space (3) of 6 mm in diameter allowing access to the area of the cornea to undergo treatment.

The surgical space is configured as a circular opening (2), while the corneal sponge (1) is provided with a convex curvature and radius of curvature of 8 mm to fit corneal curvature.

Photorefractive keratectomy was successfully performed with a laser system(ExciMed UV200LA, Summit Technology) to myopic patients using the corneal sponge. The surgery was performed by setting the laser mode to an ablation zone diameter of 4.5 mm, 238 pulses and an ablation rate of 0.25 μm/pulse.

The corneal sponge (1) was very useful in preventing exuded fluids from entering the surgical area, to align the cornea and to protect the remaining portions of the cornea.

EXAMPLE II

Figure 4:
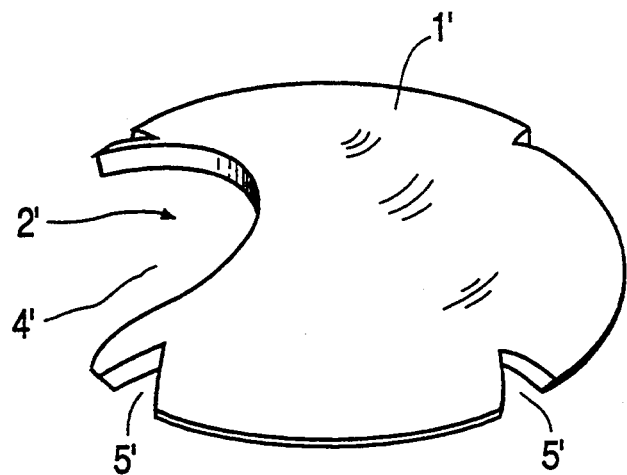
FIG.4 is a perspective view of another embodiment of the corneal sponge of the present invention.
Figure 5:
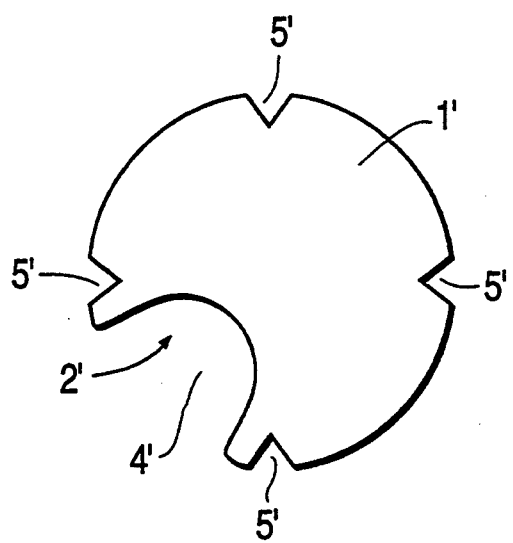
FIG.5 is a flat view thereof.

FIG. 4 and FIG. 5 depict a corneal sponge (1') having a surgical space (4') on the perimeter of the corneal sponge. The surgical space (4') is cut away from the perimeter (2') the sponge.

Pterygium surgery was successfully perfomed on the exposed area of the cornea within the surgical space of the sponge (1'). The exuded tears and ophthalmic solutions were prevented from entering the surgical area of the cornea allowing the operation to be successfully completed.

EXAMPLE III

An ophthalmic balanced salt solution(BSS PLUS, Alcon Surgical,Inc.) was cooled to 4 degrees Centigrade prior to use. The sponge (1) served as a reservoir for the solution. The corneal sponge lowered the rabbit corneal surface temperature from 36.8 to 22 degrees Centigrade prior to laser surgery. The temperature increased about 2 degrees Centigrade after 300 pulses on a 4.5 mm corneal ablation zone diameter with an ablation rate of 0.25 μm/pulse.

The postoperative corneal haze was apparently less than in the ordinary laser keratectomy.

The corneal surface temperature was measured by a radiation thermometer.

The corneal sponge containing the cooled ophthalmic solution prevented the inflammatory tendency by maintaining a lowered corneal temperature of the eye undergoing laser keratectomy.

Although a preferred embodiment of the present invention has been described, it is to be understood that other embodiments may exist and changes made without departing from the spirit and scope of the invention.

What is claimed is:

1. A corneal sponge, comprising:
    only material having liquid absorbing properties having an opening providing access to a cornea for laser treatment, and
    at least one positioning mark for target alignment of a microscopic targeting field of a laser instrument.

2. A corneal sponge as in claim 1, wherein said material having liquid absorbing properties is convex in configuration having a radius of curvature of approximately 7-8 mm and being approximately 11 mm in diameter.

3. A corneal sponge as in claim 1, wherein said material having liquid absorbing properties is selected from the group consisting of plastic sponge, cellulose, blotting paper, cotton, carbon fiber and polymeric absorbent.

4. A corneal sponge as in claim 1, wherein said positioning mark comprises a notch in said material having liquid absorbing properties, said notch being located on a periphery of said material having liquid absorbing properties.

5. A corneal sponge as in claim 1, wherein said positioning marks are four in number, each said positioning mark comprising a notch in said material having liquid absorbing properties, each said notch being located on a periphery of said material having liquid absorbing properties and spaced apart from each other by 90 degrees.

6. A corneal sponge as in claim 1, wherein said opening is geometrically in a center of said material having liquid absorbing properties and approximately 6 mm in diameter.

7. A corneal sponge as in claim 1, wherein said opening is located along a periphery of said material having liquid absorbing properties.

8. A method of using a corneal sponge having a surgical space and a positioning mark, comprising the steps of:
- positioning the sponge directly on a cornea of an eye of a patient,
- aligning the sponge utilizing the positioning mark,
- conducting laser surgery on an exposed surface of the cornea through the surgical space of the sponge, and
- absorbing fluid exuded onto the corneal surface undergoing surgery using the sponge.

9. A method of using a corneal sponge having a surgical space and a positioning mark as in claim 8, further comprising the step of soaking the sponge in a cool solution of between approximately 2 and 10 degrees Centigrade thereby protecting the corneal surface against heat produced by the surgery.

10. A method of using a corneal sponge provided with a surgical space and a positioning mark as in claim 9, wherein the step of soaking includes the step of protecting the corneal surface against heat produced by the surgery being laser photoablation.

* * * * *

UNITED STATES PATENT AND TRADEMARK OFFICE
CERTIFICATE OF CORRECTION

PATENT NO. : 5,368,590
DATED : November 29, 1994
INVENTOR(S) : S. Itoh

It is certified that error appears in the above-indentified patent and that said Letters Patent is hereby corrected as shown below:

Col. 3, line 43, delete "Is" and insert --is--.

Col. 4, line 7, delete "perfomed" and insert --performed--.

Col. 5, line 11, delete "surface" and insert --area--.

Col. 6, line 1, delete "the" and insert --a--.

Signed and Sealed this

Eleventh Day of April, 1995

Attest:

BRUCE LEHMAN

*Attesting Officer*     *Commissioner of Patents and Trademarks*